Figure 4:
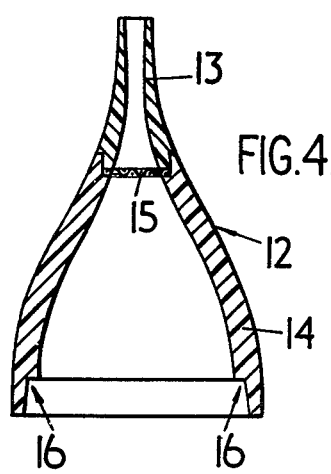

United States Patent [19]
Hodgson et al.

[11] 4,190,542
[45] Feb. 26, 1980

[54] DISPOSABLE COLUMN

[75] Inventors: Martin E. Hodgson, Harlow; Graham D. Munro, Buntingford; David P. Rickman, Ware; Jack Fennimore, Welwyn, all of England

[73] Assignee: Smith & Nephew Research Ltd., Harlow, England

[21] Appl. No.: 677,826

[22] Filed: Apr. 16, 1976

Related U.S. Application Data

[63] Continuation of Ser. No. 491,329, Jul. 24, 1974, abandoned.

[30] Foreign Application Priority Data

Jul. 26, 1973 [GB] United Kingdom ............... 35678/73

[51] Int. Cl.² ............................................. B01D 27/02
[52] U.S. Cl. .................................. 210/282; 128/214 R; 210/289; 210/293; 210/446; 210/506; 210/DIG. 23
[58] Field of Search ............... 210/237, 282, 283, 289, 210/291, 445, 446, 453, 506, DIG. 23; 128/214 R, 214.2

[56] References Cited

U.S. PATENT DOCUMENTS

| 742,254 | 10/1903 | Stern | 210/453 X |
|---|---|---|---|
| 1,664,435 | 4/1928 | Smith | 210/282 |
| 2,682,268 | 6/1954 | Ryan et al. | 128/214 R |
| 3,169,112 | 2/1965 | Nelson | 210/282 X |
| 3,224,586 | 12/1965 | Wade | 210/282 |
| 3,507,395 | 4/1970 | Bentley | 128/214 R X |
| 3,593,854 | 7/1971 | Swank | 210/445 X |
| 3,630,683 | 12/1971 | Robb | 210/282 X |
| 3,747,767 | 7/1973 | Hankammer | 210/282 |
| 3,888,250 | 6/1975 | Hill | 128/214 R |

*Primary Examiner*—Robert H. Spitzer
*Attorney, Agent, or Firm*—Robert L. Goldberg; David G. Conlin

[57] ABSTRACT

An internally smooth disposable column, of various sizes up to 800 ml. internal volume, made of biocompatible polymer is filled with particulate absorbent, e.g. carbon coated with polyHEMA, between support means located as close as practicable to inlet and outlet. L/D ratio is usually 1.5:1–5:1. Various shapes e.g. double frustoconical or trochoid of revolution are proposed for the column, which is preferably symmetrical to facilitate moulding of identical column halves; these shapes usually converge to meet a funnel-shaped connecting piece at inlet and outlet.

10 Claims, 6 Drawing Figures

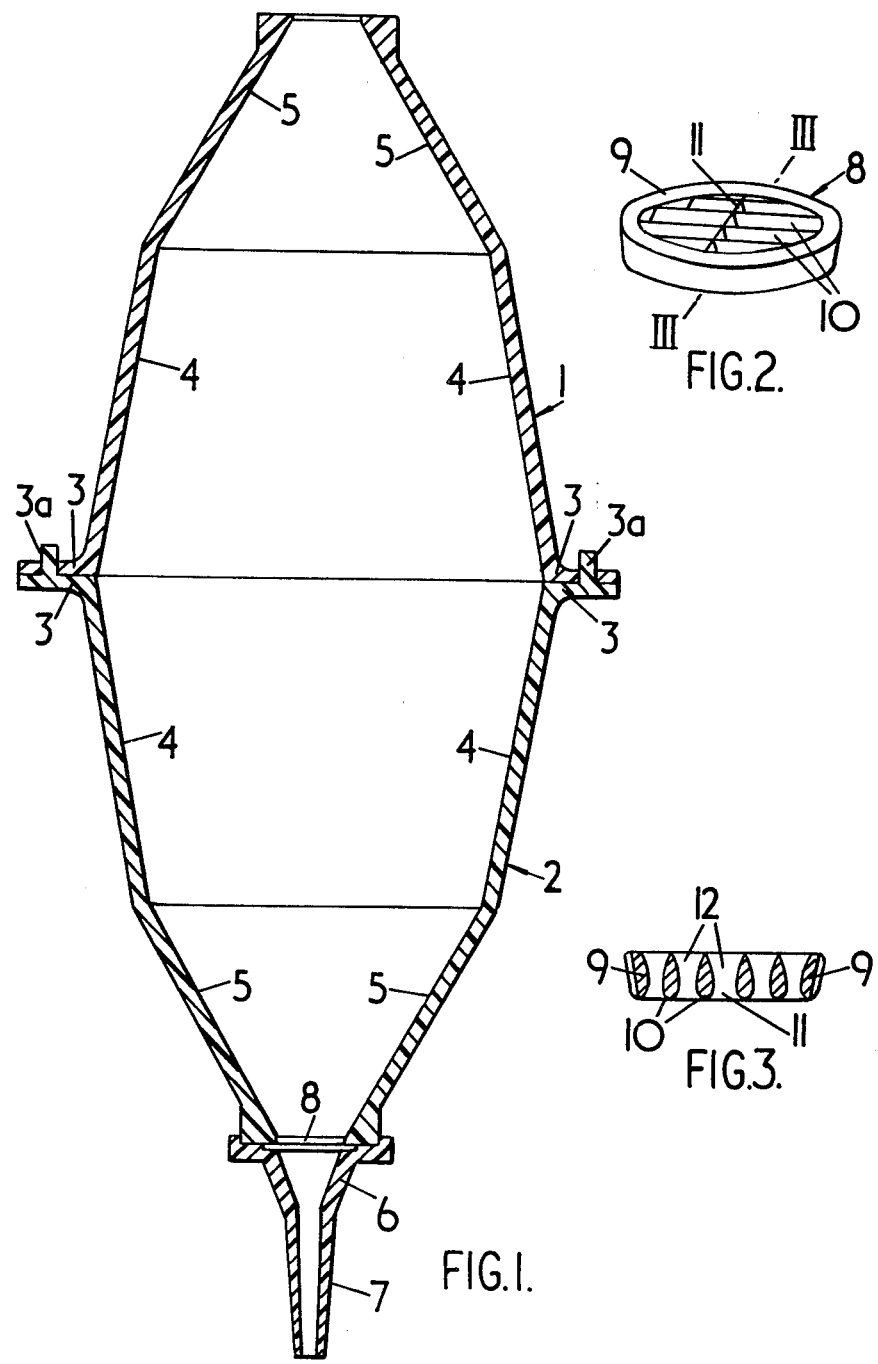

DISPOSABLE COLUMN

This is a continuation of application Ser. No. 491,329 filed July 24, 1974, now abandoned.

The present invention relates to the detoxification of blood, and more especially to a disposable column for holding a particulate absorbent, through which column blood can be passed to rid it of, for instance, barbiturates or other poisons.

Blood is a complex fluid which presents many problems in circulation through equipment outside of the body. Thus, if the blood flows too slowly, whether as a body of fluid or because of any stagnant zones in the equipment used, it will tend to clot and lead to "red thrombus". Conversely, if the blood flows too quickly through the equipment white cells become damaged leading to "white thrombus". This can also arise from turbulence in the equipment, caused for example by sharp edges in the walls of the column or like container or on the absorbent itself. Also, surfaces in contact with the blood can cause platelet adhesion and a drop in platelet count.

The present invention provides an internally smooth disposable column formed in biocompatible synthetic polymer material, filled with absorptive particulate material located between support means and provided with inlet and outlet ports the construction being such that the non-absorbing dead spaces between said ports and the nearer support means are minimised.

The length: maximum diameter ratio for columns according to the invention is preferably from 1.5:1 to 5:1. A suitable size for use with adults is about 600–800 ml internal volume, e.g. about 700 ml., holding about 300 g. of carbon and a blood hold-up of about 300 ml. Smaller sizes, e.g. from 50–400 ml. are suitable for children; also, the nature of the material to be absorbed has an influence upon the overall size of the column.

The present invention in one more particular form provides such a column comprising two identical halves located end to end, each half having a first frusto-conical tapering portion and a second frusto-conical tapering portion integral with the first and of greater (included) angle tapering to a liquid flow connection at each end of the column.

The preferred included angle of the first portion is from 10° to 30°, and of the second portion from 50° to 70°. Preferred ranges are from 17° to 22° and from 60°–65° respectively.

A further form of the invention provides such a column the internal shape of which is that of a trochoid of revolution, it being understood that the axis of revolution can be either the axis of generation of the trochoid or an axis parallel thereto.

Preferably in either of the above columns a connecting piece is located at each end, this connecting piece being funnel-shaped and defining the said dead space, and generally forming a continuation of the said second portion (or of the trochoidal surface) and terminating in a connecting stem.

The columns described above may readily be injection moulded in two identical halves from a suitable biocompatible synthetic polymeric material such as a non-toxic grade of polypropylene or ethylene/propylene copolymer, and then welded together. It may also be blow moulded as a whole column, or machined from polycarbonate.

To facilitate joining the two halves together there may be provided peripheral flanges extending around the open end of each half, provided if desired with locating male and female members, which flanges may subsequently be welded together.

The volume defined within the connecting piece can be closed off by a support grid (constituting the support means) for particulate absorbent carbon, which grid may be fixed across the broader end of the funnel-shaped connecting piece. The grid may be formed as a simple gauze or cloth, but is preferably a moulding of synthetic polymeric material where each component transverse to the flow, that is to say each grid bar, is an aerofoil shape in vertical cross-section. This ensures that blood flowing through the grid (where the velocity is relatively high) is not subject to undue turbulence.

A further more particular form of the invention provides such a column wherein a tubular central portion is provided at each end with a cap smoothly converging to an inlet or outlet connection. Preferably the cap itself is in two parts, holding between themselves the support means, such as a stainless steel (or synthetic polymer) grid, around its margins.

A still further form of the invention provides such a column which consists of a sheet of synthetic polymer material formed with a relatively deep depression communicating smoothly with two relatively shallow depressions in communication with opposite edges of the sheet, a further portion of the sheet being folded over the depressions and sealed whereby these jointly define the interior of the column; and support grids being located across each relatively shallow depression to define said dead space between themselves and the nearer sheet edge.

The invention is concerned with such columns filled wholly or partly with a particulate absorbent, especially activated carbon, (e.g. of mesh size up to 40, such as Sutcliffe Speakman grade 610, 5–10 mesh) but possibly polystyrene granules e.g. Rohm and Haas grade XAD2, XAD4, or XAD7. The packing is generally such that the absorbent granules do not move relatively in use to any significant extent. Moreover, such a filled column in a sterile, disposable form already primed with isotonic saline or plasma expander, i.e. ready for emergency use, is another important aspect of the invention. It is particularly valuable if the absorbent such as carbon is free from fines and impurities, because such material is more useful in a medical context. An especially preferred form of carbon is particulate absorptive carbon the particles of which are provided with a protective layer over or at the particle surface, usually formed by evaporation of a solution of a biocompatible polymer, such layer being resistant to mechanical breakdown, and providing a smooth permeable particle surface without plugging the pores of the material. Suitable biocompatible permeable polymers are poly(hydroxyethylmethacrylate) (polyHEMA), cellulose acetate, polyurethane, polyamide, silicone resins, etc. The amount of polymer present may be up to 20% w/w of carbon, a preferred amount being from 1 to 10% w/w, or more preferably 0.25 to 5% e.g. 3% w/w. The particles may also contain a prior impregnation of the same or a different biocompatible polymer. In a possible method of preparing such a carbon a heated mass of carbon particles (possibly themselves polymer-impregnated and preferably washed free of fines by an upwardly flowing current of liquid) the individual members of which carbon particles are caused or allowed to adopt relative motion are sprayed with a solution of the biocompatible polymer (e.g. aqueous ethanolic polyHEMA) in an amount such that solvent evaporates leaving a coating over, or at, each particle surface.

The relative motion can be achieved by tumbling over an inclined surface, e.g. while heated with hot air at for example 30°–100° C.

The present invention, while it is primarily concerned with the empty or filled column, also envisages a method of detoxification of blood using such a column.

Figure 5:
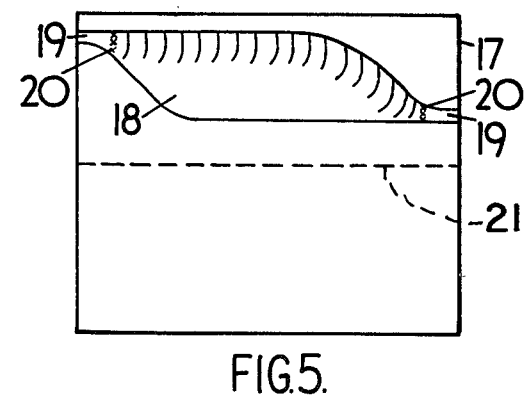
Figure 6:
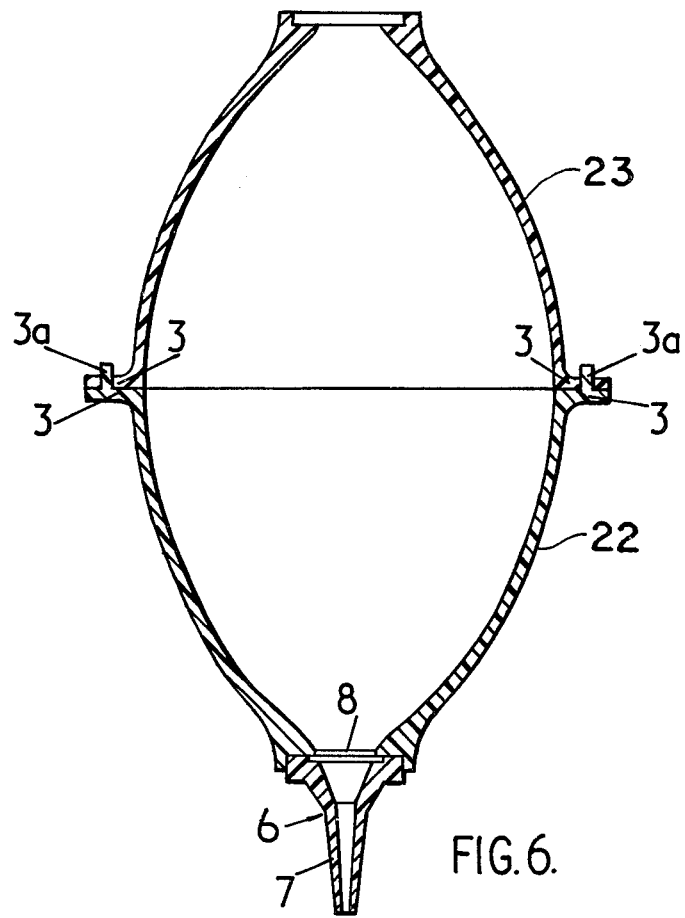

The invention will be further described with reference to the accompanying drawings, in which:

FIG. 1 is a vertical diagrammatic section through a column according to the invention;

FIG. 2 is a perspective view of an internal retaining grid for carbon or like absorbent within such a column, FIG. 3 is a section along the line III—III of FIG. 2, FIG. 4 is a diagrammatic section through part of another column, FIG. 5 is a top view of a formed sheet which can be folded to a column according to the invention, and FIG. 6 is a vertical diagrammatic section through another shape of column according to the invention.

The column shown in FIG. 1 consists of two identical somewhat cup-shaped halves 1 and 2 joined by welding around their larger openings. Each cup-shaped half has a surrounding flange 3, a first tapering portion 4, and a second tapering portion 5 which where they meet are smoothly radiused to avoid discontinuities. A funnel-shaped connecting piece 6 welded to the column leads to a connecting stem 7, both this and the previous welds being carefully carried out and inspected to ensure that no molten polymer has intruded from the weld into the column. Since the column is circular in cross-section, each of the portions 4 and 5 are frusto-conical; the included angle of the second portion 5 is greater than that of the first portion 4, while the funnel-shaped piece 6 is generally a continuation of the second portion. In the preferred embodiment these included angles are 19°–20° for the first portion 4 62° for the second portion 5.

A support grid 5 of 14 mm diameter for absorbent carbon granules is fixed over the wide end of funnel-shaped connecting piece 6 in the lower half 2 with a similar grid (not shown) being located at the top end. The dead space or volume thereby defined is thus very small, since the converging funnel region is only of the order of 15 mm long. (In general the ratio of grid diameter to length of converging portion ranges from 0.5:1 to 2:1. The funnel can be slightly flared rather than be straight-line convergent). The whole column is joined together at the flanges 3 by complementary projections and holes as at 3a, where it is sealed e.g. by heat or ultrasonics or solvent welding, and thereafter filled with carbon as described in more detail below. The stem 7 of the lower half is the inlet.

The sizes and shapes of the funnel-shaped portion and its relationship to and union with the column, together with the size of the absorbent particles lying on, and supported over the holes of, the grid all affect the amount of shear on the blood and the nature of the blood flow. In general shear rate maximum is less than 1000 seconds$^{-1}$.

The shape of the column is such as to reduce turbulent flow. In theory the two halves need to be differently shaped. However, the shape as shown especially when smoothly rounded internally can be injection-moulded from a single mould since the two halves are identical, and is a good compromise of the various factors to be taken into consideration. Moreover, it can be used either way up, and the weight of carbon is supported on the convergent walls rather than on the grid.

The absorbent to be filled into the column through the top end prior to attachment of an outlet piece as at 7 may be any known particulate absorbent but is preferably that form of coated carbon described above. Afer filling, such a column is preferably primed with physiological saline, outgassed, sealed, overwrapped, and sterilised, e.g. by steam autoclaving or hard gamma rays (Cobalt 60). The column may be primed to contain degassed isotonic saline or plasma expander.

Material for the support is a woven or moulded nylon grid. Alternatively a specialised form of synthetic plastics grid can be used. A typical plastics grid 8 is shown in perspective in FIG. 2. It is moulded as a surrounding tapered ring 9 with integral parallel ribs 10 and a transverse rib 11 defining between them spaces 12 which do not allow passage of the carbon granules. Each rib 10 and 11 is aerofoil-shaped (or "tear-drop" shaped) in vertical cross-section to minimize turbulence in this relatively narrow flow passage.

The column halves 1 and 2 may be injection-moulded for example in polypropylene, polycarbonate, or any other fairly rigid biocompatible polymer. The whole article accordingly lends itself to manufacture as a production basis and can be thrown away after use.

In a specific test, such a column (as shown in FIG. 1 i.e. with the lower opening closed by the funnel 6) was filled through the top opening with 300 g of polyHEMA coated activated charcoal (Sutcliffe Speakman 610, 5×10 mesh, with a 4% spray coating of polyHEMA). The upper funnel piece, (not shown) was thereafter welded into place and the lower end of the filled column was capped, and the assembly lead-tested under water. The column was connected to a priming reservoir containing 0.9% saline and filled under vacuum so that any air therein was displaced. Finally, it was sterilised by steam autoclaving.

This column was used for an 'in vitro' run in the laboratory, in which a saline solution of pentobarbital was pumped through the column. The following data was noted:

Duration of run: 4 hours
Flow rate: 200 ml/min
Inlet concentration of pentobarbitone solution: 12 mg
Pressure drop across column: 7.4 mm Hg
Wt. of pentobarbitone removed in 4 hours: 1.6

In FIG. 4, a polycarbonate cap 12 consists of two parts 13 and 14 holding between themselves a stainless steel grid 15. The cap fits by joint 16 over one end of a tubular polycarbonate column (not shown). The space between grid 15 and the narrow end of part 13 itself dimensioned to accept standard haemodialysis tubing) is minimal. The various parts fit to define a smooth internal surface.

One such end cap was assembled to a length of polycarbonate tubing 41 cm in length. This was now filled with 300 g of polyHEMA coated charcoal (Sutcliffe Speakman 610, 5×10 mesh, spray coated with 3% by weight of polyHEMA). The second cap was then assembled, with solvent welding, to the open end of the column. Care was taken to ensure that all the available space between the two end caps was filled with the charcoal.

The assembled, filled column was primed with saline solution using a high-speed flush-through to eliminate air. The lower end of the column was closed by a screw-on cap, and the column, with a second cap, was sealed into a nylon/polypropylene film bag full of saline. This was placed into an autoclave and sterilised by heating for 1 hour at 116° C.

After cooling, the open end of the column was sealed by manipulating its cap into position from outside the bag. The bag was then opened and the column used for an 'in vivo' run with a pig.

For the 'in vivo' run, a 30 kg pig was anaesthetized, and the column connected via tubing and cannulae to the jugular vein. Using a peristaltic blood pump, the flow rate of blood through the column was increased to 196 cm³/min. Pressure drop across the column was 59 mm Hg. 11.875 cm³ of blood were perfused through the column over a period of 90 minutes. At the end of the run the column was disconnected, rinsed and dismantled. The entire column was found to be free of clots and thrombus formation. Only one small thread-like clot was found attached to the bottom filter mesh.

In FIG. 5, a white 24-mil-thick pigmented sheet 17 of polystyrene was vacuum-formed with a relatively deep depression 18 and two shallower depressions 19 communicating with opposite edges of the sheet and each containing a stainless steel grid 20.

Polystyrene blood ports, from renal dialyser components, were solvent welded into position in the inlet and outlet depressions 19 of the form. The depression 18 was filled with activated charcoal (Sutcliffe Speakman 610, 5×10 mesh, 3% impregnation plus 3% spray coating of polyHEMA). The sheet was then folded over along the dotted line 21 to form a lid, which was solvent welded in place. This closed the device except for the inlet and outlet ports, which were sealed by small caps. The device was irradiation sterilised using 'hard' gamma rays from a Cobalt 60 source.

In FIG. 6 two identical halves 23 and 22 fit together to provide a smoothly rounded internal surface.

As shown, this surface is generated by forming a trochoid (that curve formed by the path of a point within the circumference of a circle rolling on a straight line) and rotating it around an axis along or parallel to the said straight line.

Flange 3, locating members 3a, funnel-shaped piece 6, stem 7 and grid 8 are the same as in FIG. 1 and thus bear the same reference numerals.

The above description discusses in some detail a trochoidal column, a cylindrical column and a column having regions of different taper. It is also possible to have columns of other shapes, e.g. as an ellipsoid, or as a simple biconical shape.

The major properties of each geometry may be summarized.

| Column | Non-returned Volume cm³ | Stagnant Volume cm³ | L/B ratio | Mixing Zone |
|---|---|---|---|---|
| 1. FIG. 1 | 31.4 | 5.8 | 2.47 | 1.18 |
| 2. Trochoid (FIG. 6) | 30 | 1.2 | 1.76 | 1.3 |
| 3. Ellipsoid | 37.5 | 4.9 | 1.50 | 1.34 |
| 4. Conical | 52.8 | 27.9 | 1.55 | 1.48 |

The mixing zone values represent the number of interstitial volumes occupied by the mixing zone. The whole of the column consists of a mixing zone.

It can be seen that those geometries with the least stagnant volumes are gradual in shell angle changes. However, the present designs of such geometries have had low length/diameter ratios such appear to lead to bigger deviations from plug flow and hence larger non-returned volumes.

We claim:

1. Disposable haemoperfusion equipment comprising:
   (A) a column,
     (i) formed in biocompatible synthetic polymer material,
     (ii) having a smooth internal surface,
     (iii) enclosing perforate internal support means towards each end of said column
     (iv) diminishing in diameter from a maximum diameter intermediate said ends, and then
     (v) converging smoothly at each end of said column to an inlet port and an outlet port respectively, each such port defining a minimal dead space between itself and the nearer support means,
     (vi) said column having a length to maximum diameter ratio of 1.5:1 to 5:1 and an internal volume of 50 to 800 ml., and
     (vii) said column being formed as two identical halves located end to end, each half possessing a first frusto-conical tapering portion having an included angle of from 10° to 30°, and a second frusto-conical tapering portion, integral with said first portion, but of an included angle of from 50° to 70°, tapering to a liquid flow connection at each end of said column;
   (B) a body of absorbtive particulate material,
     (i) substantially filling the column and held between the support means so that the particles do not move relatively in use, and
     (ii) consisting of particles having a smooth biocompatible surface; and
   (C) a biocompatible liquid charge filling the column, chosen from the group of degassed isotonic saline and plasma extender.

2. Haemoperfusion equipment as claimed in claim 1 of internal volume from 600 to 800 ml.

3. Haemoperfusion equipment as claimed in claim 1, having an internal volume from 50 to 400 ml.

4. Haemoperfusion equipment as claimed in claim 1, wherein the included angle of the first portion is from 17° to 22° and that of the second portion is from 60° to 65°.

5. Haemoperfusion equipment as claimed in claim 1 wherein the column has a funnel-shaped connecting piece at each end defining the dead space.

6. Haemoperfusion equipment as claimed in claim 5, wherein the dead space is closed by a support grid fixed across the broader end of the funnel-shaped connecting piece.

7. Haemoperfusion equipment as claimed in claim 6, wherein the ratio of grid diameter to length of the converging portion ranges from 0.5:1 to 2:1.

8. Haemoperfusion equipment as claimed in claim 1, wherein the absorbent is a particulate absorptive carbon the particles of which are provided with a protective layer of a biocompatible polymer resistant to mechanical breakdown and providing a smooth permeable particle surface without plugging the pores of the material.

9. Haemoperfusion equipment as claimed in claim 8 wherein the biocompatible coating polymer is poly(hydroxyethylmethacrylate) in an amount of 0.25 to 5% w/w of the carbon.

10. Disposable haemoperfusion equipment, comprising:

(A) a column, the internal shape of which is that of a trochoid of revolution,
  (i) formed in biocompatible synthetic polymer material,
  (ii) having a smooth internal surface,
  (iii) enclosing perforate internal support means towards each end of the column,
  (iv) diminishing in diameter from a maximum diameter intermediate said ends, and then
  (v) converging smoothly at each end of said column to an inlet port and an outlet port respectively; each such port defining a minimal dead space between itself and the nearer support means,
  (vi) said column having a length to maximum diameter ratio of 1.5:1 to 5:1 and an internal volume of 50 to 800 ml;
(B) a body of absorbtive particulate material,
  (i) substantially filling the column and held between the support means so that the particles do not move relatively in use, and
  (ii) consisting of particles having a smooth biocompatible surface; and
(C) a biocompatible liquid charge filling the column, chosen from the group of degassed isotonic saline and plasma extender.

* * * * *